United States Patent [19]
Levin

[11] Patent Number: 5,667,526
[45] Date of Patent: Sep. 16, 1997

[54] TISSUE RETAINING CLAMP

[76] Inventor: John M. Levin, 412 Fairview Rd., Narberth, Pa. 19072

[21] Appl. No.: 524,496

[22] Filed: Sep. 7, 1995

[51] Int. Cl.$^6$ .................................................. A61B 17/00
[52] U.S. Cl. ........................ 606/207; 606/205; 606/151; 81/418; 81/424.5
[58] Field of Search .................... 606/205, 207, 606/208, 151, 210, 211, 158, 157; 81/418, 420, 424.5, 426, 426.5; 128/751, 749; 227/175.1

[56] References Cited

U.S. PATENT DOCUMENTS

| | | | |
|---|---|---|---|
| 3,694,834 | 10/1972 | Daniels, Jr. | 81/426.5 |
| 4,064,881 | 12/1977 | Meredith. | |
| 4,509,517 | 4/1985 | Zibelin. | |
| 4,519,392 | 5/1985 | Lingua. | |
| 4,856,518 | 8/1989 | McFadden. | |
| 5,275,615 | 1/1994 | Rose | 606/208 |
| 5,373,854 | 12/1994 | Kolozsi | 606/208 |
| 5,394,885 | 3/1995 | Francese | 606/207 |
| 5,423,471 | 6/1995 | Mastri et al. | 227/175.1 |
| 5,452,837 | 9/1995 | Williamson, IV et al. | 227/19 |
| 5,522,839 | 6/1996 | Pilling | 606/207 |

FOREIGN PATENT DOCUMENTS

| | | | |
|---|---|---|---|
| 1827191 | 6/1993 | U.S.S.R. | 606/207 |

OTHER PUBLICATIONS

Jarit Instrument Update, Jun. 1991.

*Primary Examiner*—Jeffrey A. Schmidt
*Attorney, Agent, or Firm*—Caesar, Rivise, Bernstein, Cohen & Pokotilow, Ltd.

[57] ABSTRACT

A surgical clamp has pivoting jaws with undulating arrays of teeth that are interdigitating and offset with relation to each other. This clamp structure assures a firm, non-slipping grip in the presence of blood and body fluids during surgery. The inner surfaces of the jaws are concave to allow the clamp to grasp more tissue or organ that would be possible with flat inner surfaces. Laparoscopic and open surgery embodiments are included. An alternative to the embodiment is a clamp having openings through which tissue or an organ can protrude to allow an even greater amount of tissue or organ to be grasped.

7 Claims, 5 Drawing Sheets

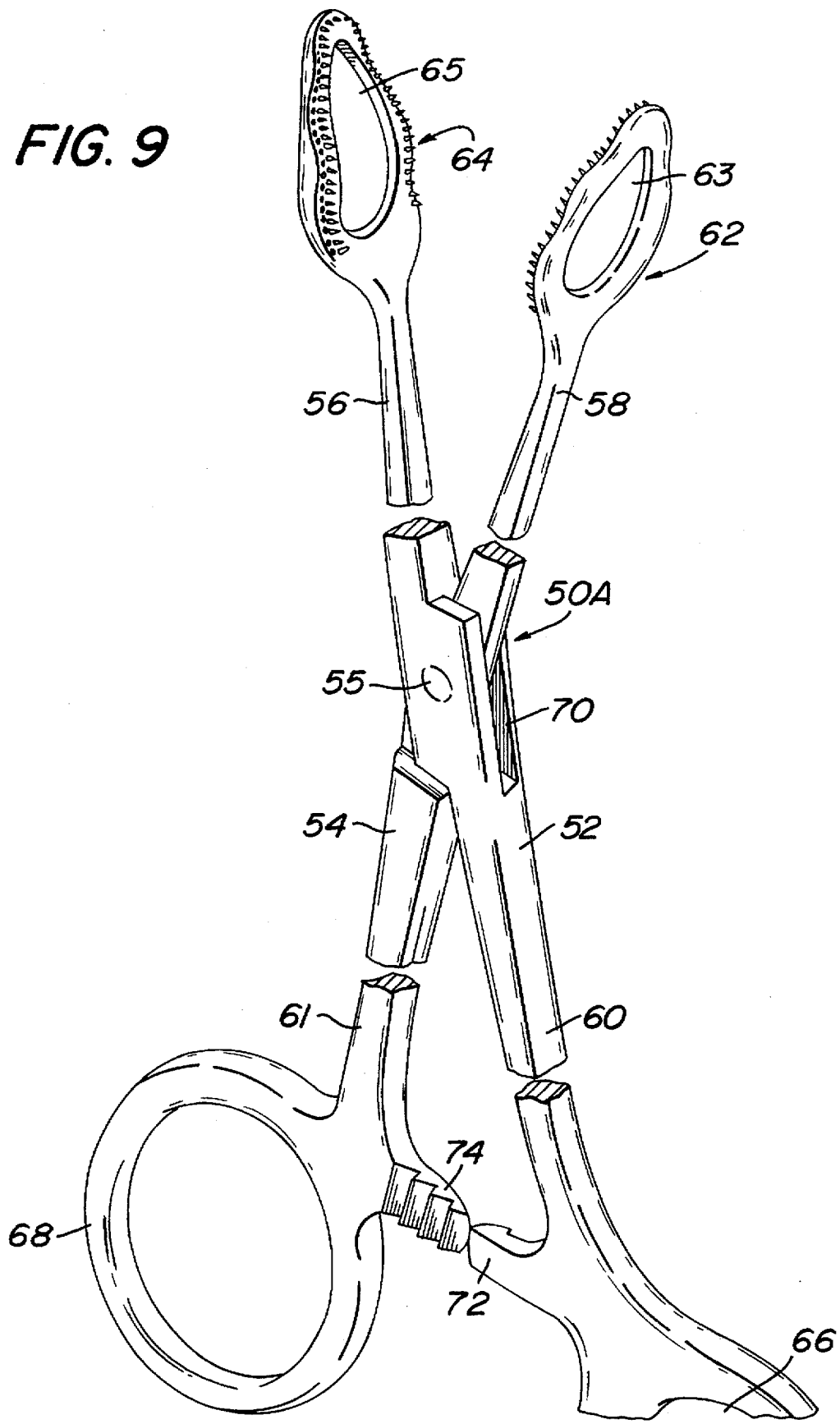

5,667,526

TISSUE RETAINING CLAMP

BACKGROUND OF THE INVENTION

This invention relates generally to the field of surgical clamps for tissues or organs, and more particularly to clamps that can be used during laparoscopic or other surgery for holding body tissues and organs firmly.

U.S. Pat. No. 5,304,183 (Gourlay, et al.) discloses a laparoscopic spring biased clamp inserted through a trocar. An applicator applies the clamp and releases and removes the clamp.

U.S. Pat. No. 4,856,518 (McFadden) discloses a laparoscopic clamp with an applicator for opening and closing a clamp which is levered and provides rotation for the clamp application portion.

U.S. Pat. No. 4,064,881 (Meredith) discloses an abdominal clip and applicator with upper and lower teeth spaced apart and not in contact with each other when the clamp is closed.

A problem often exists in surgery in that the clamps often slip due to the amount of fluids, blood and other foreign matter in the area of surgery, or due to the fact that in extracting or dislodging tissues or organs a large force is often applied. Therefore, there is a need for surgical clamps for laparoscopic or open surgery which provide for increased and more positive gripping of the tissue or organ to insure a firm non-slipable hold during surgical operations.

OBJECTS OF THE INVENTION

Accordingly, it is the general object of the instant invention to provide a surgical clamp for laparoscopic or other surgery which improves upon, and overcomes the disadvantages of the prior art.

It is a further object of the instant invention to provide a surgical clamp for a laparoscopic or other surgery which provides a firmer grip on clamped tissues or organs that is available with existing surgical clamps.

It is still a further object of the instant invention to provide a surgical clamp for laparoscopic or other surgery which allows for the firm clamping of a large volume of body tissues or organs.

It is yet a further object of the instant invention to provide surgical clamp for laparoscopic or other surgery which has an upper jaw and a lower jaw, each having a set of inter-digitating teeth.

It is still yet a further object of the instant invention to provide a surgical clamp for laparoscopic or other surgery which has upper and lower jaws with indentations for accepting the teeth of the opposing jaw when the jaws are clamped, to increase the stability and firmness of the clamp.

It is another object of the instant invention to provide a surgical clamp for laparoscopic or other surgery which has an upper and lower jaw, each having a set of teeth which undulates in an in-and-out fashion.

It is still another object of the instant invention to provide a surgical clamp for laparoscopic or other surgery which has an upper and lower jaw each having a set of teeth which undulates in an up-and-down fashion transversely to the in-and-out indulation.

It is yet another object of the instant invention to provide a surgical clamp for laparoscopic or other surgery having an upper and lower jaw, each having a set of teeth with the sets offset from each other.

It is still yet another object of the instant invention to provide a surgical clamp with open jaws for clamping a greater volume of body tissues than can be clamped with closed jaws.

SUMMARY OF THE INVENTION

These and other objects of the instant invention are achieved by providing a laparoscopic clamp having opposing upper and lower jaws with a set of teeth set in each jaw. Each set of teeth undulates both in-and-out in a first, horizontal plane as well as up-and-down in planes orthogonal to the horizontal plane. In addition, the teeth of the opposing jaws are offset with respect to each other with the each set of teeth arrayed in lines parallel to each other. Each jaw also has indentations for accepting the tips of teeth of the opposing jaw so that the clamp may be more fully closed when it is operated. The tips of the teeth are blunted to prevent tearing of the tissue or organ during clamping.

The inner surfaces of the jaws of the clamp are concave in shape allowing for a larger volume of the tissue or organ to be clamped than with flat inner surfaces. A second embodiment of this invention uses jaws of the same shape and structure as the laparoscopic embodiment which are attached to forceps for open surgery. Alternatively for both embodiments, each jaw may have an opening therein to allow an even larger volume of tissue to be grasped.

DESCRIPTION OF THE DRAWINGS

These and other objects and many of intended advantages of this invention will be readily appreciated when the same becomes better understood by reference to the following detailed description when considered in connection with the accompanying drawings wherein:

FIG. 9 is an isometric view of an alternative to the second embodiment with jaws having openings.

DETAILED DESCRIPTION OF THE PREFERRED EMBODIMENTS

Figure 1:
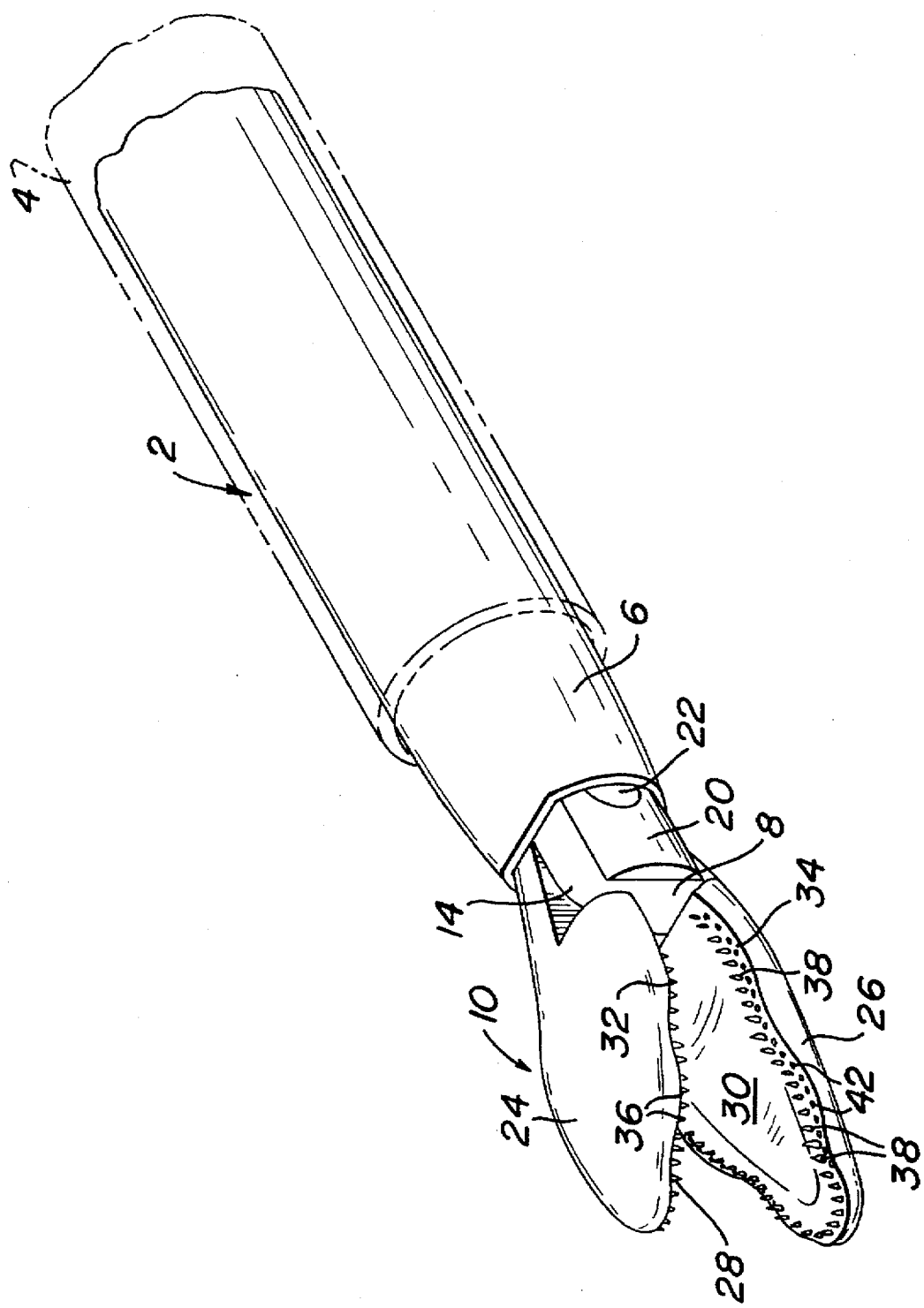
FIG. 1 is an isometric view of the laparoscopic embodiment of the clamp.

Referring now in greater detail to the various figures of the drawings, wherein like reference characters refer to like parts, there is shown in FIGS. 1–5 the first embodiment of the clamp, the laparoscopic clamp 2 constructed in accordance with this invention. The laparoscopic clamp 2 is inserted in a trocar 4. It comprises an outer cylinder 6, an inner rod 8 and a clamping member 10. The inner rod 8 has a distal end 14 with a pair of side members 20, connected to opposite sides of the inner rod 8, and a pivot pin 22, which extends into and through the side members 20 and the inner rod 8.

When the clamp 2 is inserted into the trocar 4 so that the clamp member extends pass the end 16 of the trocar 4, a biasing spring (not shown) causes the jaws 24 and 26 of the jaw member 10 to open. The jaws can be manipulated and closed by the surgeon using well known mechanisms such as triggers, rotating knobs, or scissors like finger holders which are standard and well known to those familiar with the art. Any one of these types of mechanisms can be used and do not limit the invention. In the interest of brevity, and because this invention is concerned with the structure and shape of the jaws of the clamp, further discussion of the mechanism for operating the clamp is not given.

The clamp member 10 comprises an upper jaw 24 and a lower jaw 26 which are connected to the pivot 22.

The upper jaw 24 and the lower jaw 26 each have an inner surface 28 and 30 respectively and peripheral raised shelf sections 32 and 34. The inner surfaces 28 and 30, (FIGS. 4 and 5), are concave in shape to allow for the capture of tissues or organs between the jaws when the piece is clamped. This results in firm gripping of a greater volume of tissue or organs that would otherwise be available with flat inner surfaces. In addition, the raised peripheral shelf sections 32 and 34 increase the open area between the jaws when the jaws are clamped.

Figure 2:
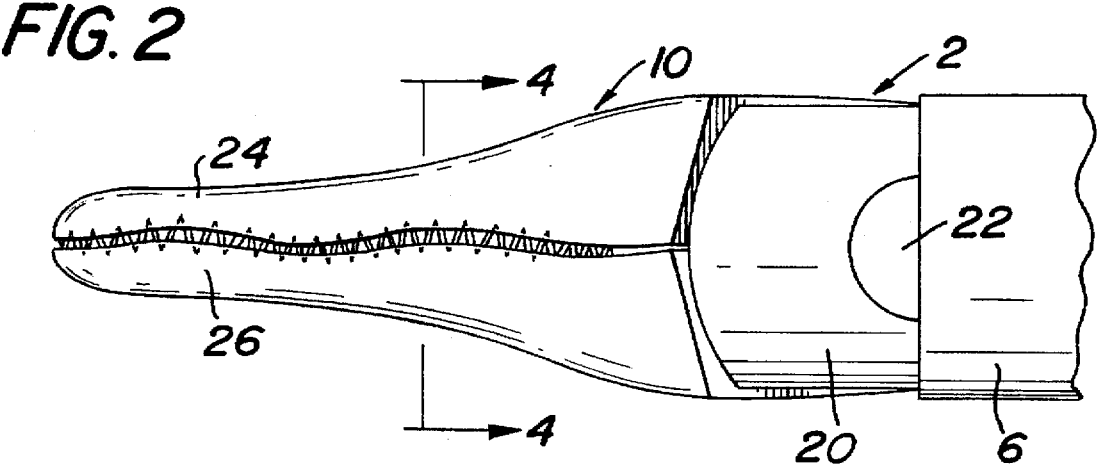
FIG. 2 is a side view of the jaws of the clamp with the jaws closed.
Figure 3:
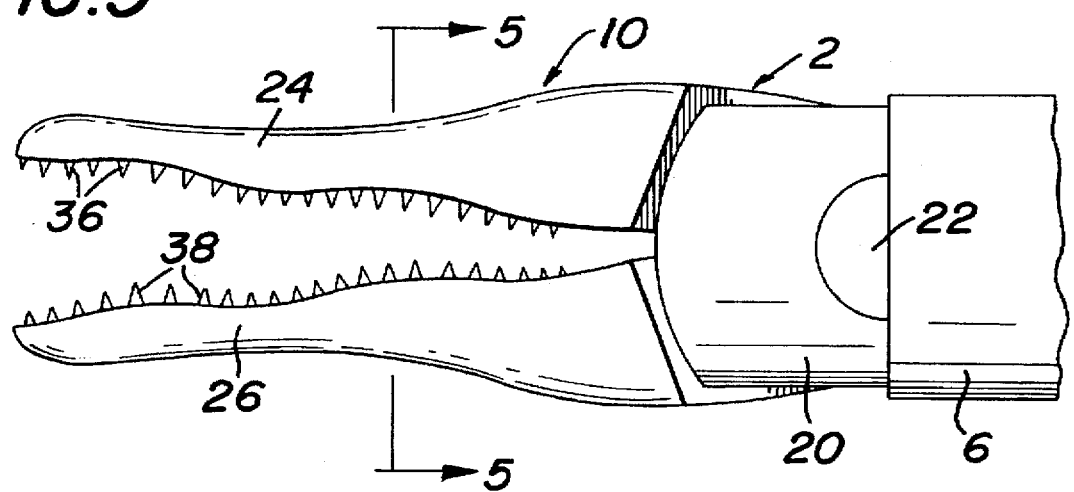
FIG. 3 is a side view of the jaws of the clamp with the jaws open.
Figure 4:
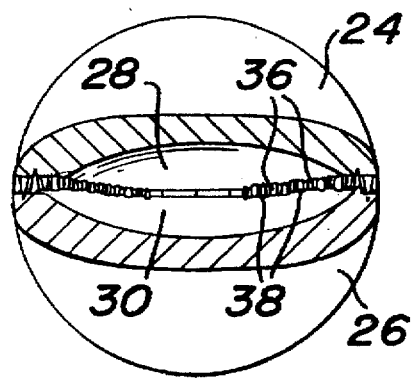
FIG. 4 is a sectional view of the clamp taken along the line 4—4 of FIG. 2.

The jaws 24 and 26 have arrays of teeth 36 and 38, respectively, positioned in the peripheral shelf sections 32 and 34. As can be seen in FIG. 1, the periphery of the jaws 24 and 26 undulate. Because the peripheral sections 32 and 34 follow the undulating shape of the jaws 24 and 36, the array of upper teeth 36 and lower teeth 38 which are set in a peripheral shelf sections 32 and 34 respectively, also undulate in accordance with the undulating shape of the periphery of the upper jaw 24 and the lower jaw 26 respectively. It also should be noted, as can be seen in FIG. 2, when viewing the jaws from the side, the peripheral shelf sections 32 and 34 also undulate in planes orthogonal to the surfaces of the peripheral sections 32 and 34. Therefore, the arrays of teeth 36 and 38 undulate in the horizontal plane of the surfaces of the peripheral self sections 32 and 34 and in the vertical plane perpendicular to the plane of the surfaces of the peripheral shelf sections 32 and 34. Thus, when the jaws 24 and 26 are closed and positioned horizontally, the arrays of teeth undulate in both an in-and-out fashion and in an up-and-down fashion relative to a horizontal plane.

Figure 5:
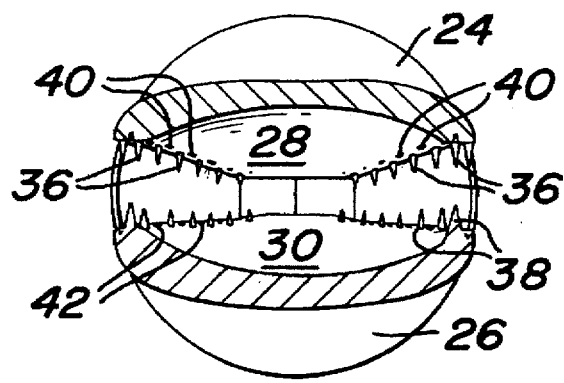
FIG. 5 is a sectional view of the clamp taken along line 5—5 of FIG. 3.

Also as can be seen in FIGS. 1, 2 and 5 the peripheral shelf sections 32 and 34 comprise an array of indentations 40 and 42, respectively, for the tips of the teeth of the opposing jaw when the jaws are clamped. When the jaws are clamped, each of the teeth of the array of upper teeth 36 and each of the teeth of the array of lower teeth 38 fits into a corresponding indentation 42 and 40 in the opposing jaw. The tips of the teeth of the arrays 36 and 38 are slightly blunted to avoid tearing the tissue that is clamped.

It also can be seen in FIG. 1, that the array of upper teeth 36 extends outside of the array of lower teeth 38 (overbite) when the jaws are clamped. Finally, it should be noted that the teeth are interdigitating, i.e. each of the teeth is positioned between two of the opposing teeth, when the jaws are closed.

Figure 6:
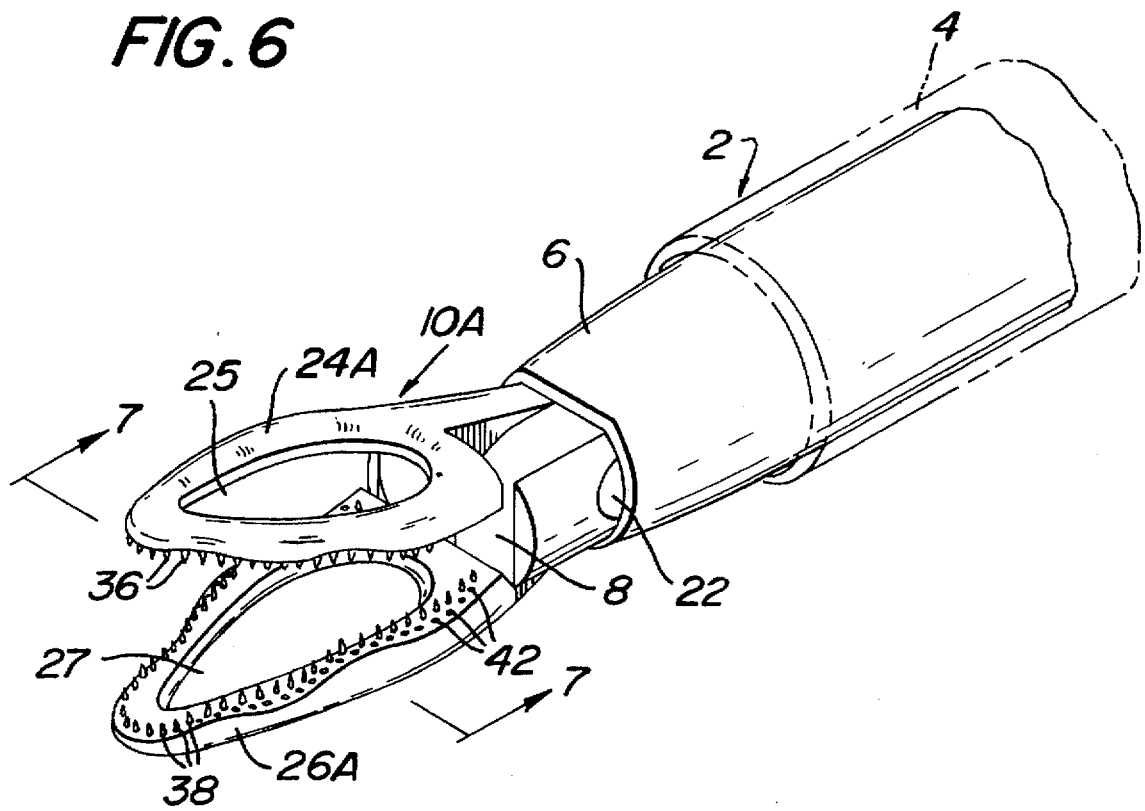
FIG. 6 is an isometric view of an alternative to the first embodiment of the laparoscopic with jaws having openings and the jaws shown in the open position.
Figure 7:
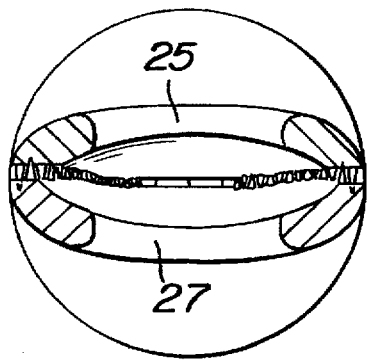
FIG. 7 is a sectional view of the clamp taken along line 7—7 of FIG. 6 with the jaws in the closed position.

An alternative to the first embodiment is shown in FIGS. 5 and 6. As can be seen in FIGS. 5 and 6, the clamps are the same as those previously described for the first embodiment as shown in FIGS. 1–5, except that the jaw member 10A comprises jaws 24A and 26A which have openings 25 and 27, respectively. The purpose of the openings 25 and 27 is to allow the clamps to firmly grasp even more tissue than would be possible with the concave surfaces 28 and 30 of the first embodiment. The grasped tissue or organ protrude through the openings 25 and 27, thus precluding the spreading and the tearing of the tissue or organ, when the jaws 24A and 26A are firmly closed.

The description of the jaws 24A and 26A in detail is not repeated here, because the remainder of the jaws 24A and 26A is the same as the jaws 24 and 26 except for the opening 25 and 27. Thus, the arrays of teeth are offset with respect to each other, there are indentations in each jaw to accept the tips of the teeth of the opposing jaw, and the arrays of teeth undulate in both an in-and-out fashion and in an up-and-down fashion as previously described for the first embodiment.

Figure 8:
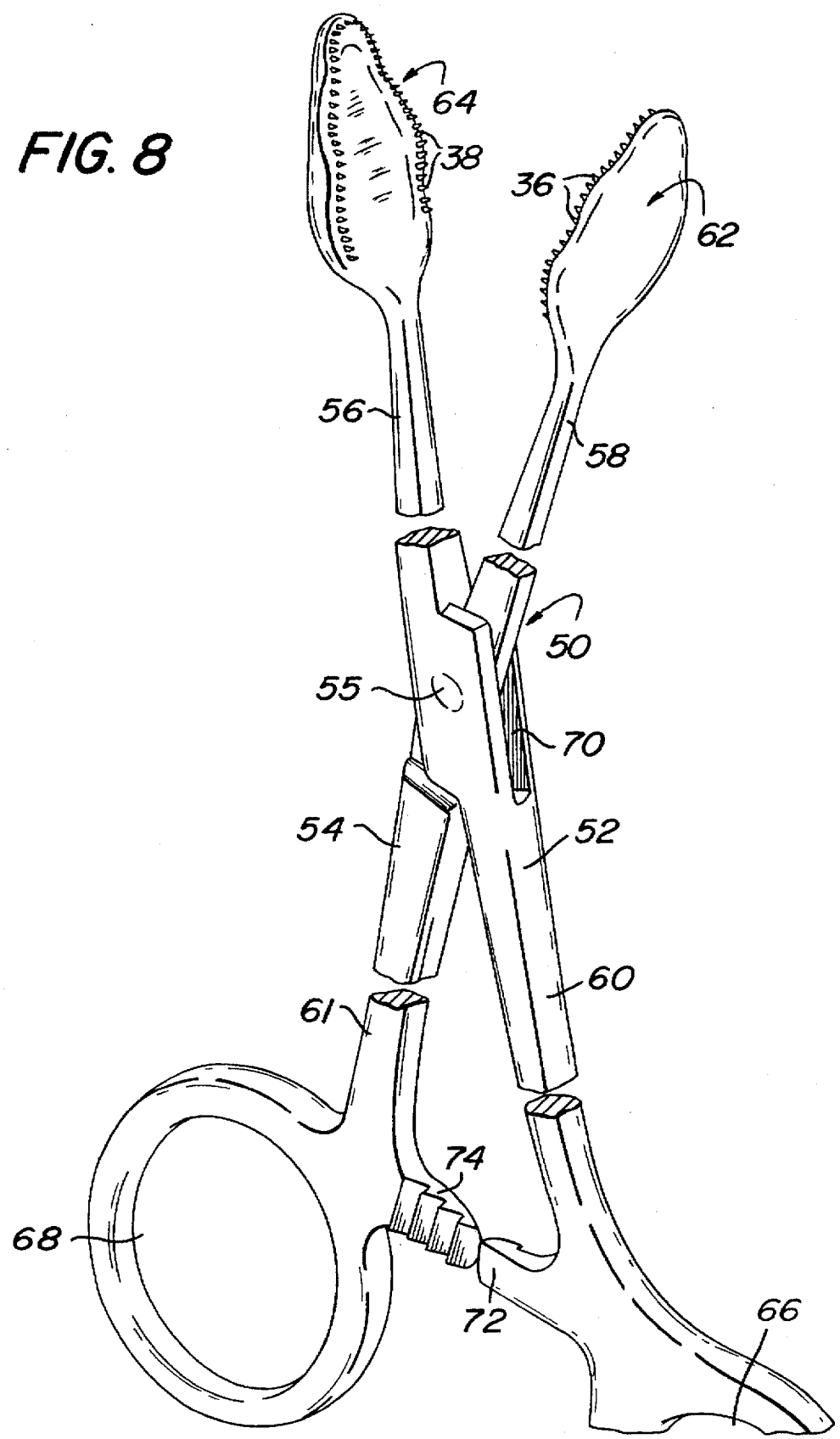
FIG. 8 is a broken away isometric view of a second embodiment, a forceps type of clamp used in open surgery.

FIG. 8 shows the second embodiment of this invention comprising a forceps 50 having a first member 52 and a second member 54 and a pivot pin 55 which pivotally connects the members 52 and 54. First member 52 and second member 54 have distal sections 56 and 58 and proximal sections 60 and 61, respectively. The members 52 and 54 also comprise clamping jaws 64 and 62 located at the distal sections 56 and 58, respectively. As in the first embodiment, each of the jaws 62 and 64 have teeth 36 and 38 respectively which undulate in-and-out a first plane parallel to the shelves upon which the teeth are installed and also up-and-down in a planes orthogonal to the first plane.

The structure of the jaws 62 and 64 is the same as the structure of the jaws 24 and 26 of the first embodiment. As in the first embodiment the jaws 62 and 64 comprise indentations, there is an overbite between the arrays of teeth, the teeth are interdigitating with respect to each other, and there is a large open area between the teeth to enable the jaws to grasp a larger volume of tissue or organ as in the first embodiment. Therefore, there is no need to repeat the description of the jaws 62 and 64 in detail since they follow the description of the jaws of the first embodiment as originally given. Suffice it to say that the jaws of the fist and second embodiments are the same except that in the second embodiment for open surgery, the jaws are made larger.

The proximal sections 60 and 61 include finger rings 66 and 68. The surgeon, by inserting his or her fingers through the finger rings 66 and 68 and moving the fingers closer or further apart can open and close the jaws 62 and 64 in scissors-like fashion. The first member 52 and the second member 54 have openings 70, which allow the first member 52 and the second 54 to rotate about the pivot pin 55 as a surgeon manipulates the jaws 62 and 64 via the finger rings 66 and 68. The proximal sections 60 and 61 also comprise extensions 72 and 74 with ratchet teeth. The ratchet teeth of extension 72 mate with the ratchet teeth of extension 74 to hold the jaws at a fixed position as desired by the surgeon.

An alternative to the second embodiment of the tissue retaining clamp is shown in FIG. 9. The only difference between this alternative and the second embodiment of FIG. 8 are the openings 63 and 65 in the jaws 62 and 64. Therefore, in the interest of brevity, the remainder of the forceps will not be described. Suffice to say, that the teeth are arrayed in each jaw in an undulating fashion as previously described with indentations in each jaw to accept the tips of the teeth of the opposing jaw and the arrays of teeth are offset from each other. The remainder of the clamp is also identical to the clamp of the second embodiment of FIG. 8.

An undulating surgical clamp for laparoscopic or open surgery has been described which has a number of unique and special features which enable the clamp to hold body tissues or organs firmly. These features include arrays of teeth set in opposing jaws which have double undulations, undulating in-and-out in a first plane and also up-and-down in a plane orthogonal to the first plane. Also, the arrays of teeth are interdigitating with respect to each other, one array of teeth is positioned outside of the second array of teeth (overbite) and the jaws of teeth have indentations accepting each of the tips of the teeth from the opposing jaws when the jaws are clamped. Finally, the teeth are set into peripheral shelves in the jaws and the inner surface of the jaws are concave which increases the area between the jaws when the jaws are clamped and which allows for a greater volume of the tissue or organ to be held within the clamp when the jaws are clamped. Alternatively the jaws may have openings to enable the grasping of even more tissue than with the concave surfaces.

Without further elaboration, the foregoing will so fully illustrate my invention, that others may, by applying current or future knowledge, readily adapt the same for use under various conditions or service.

I claim:

1. A clamp for use in laparoscopic surgery comprising a rod, an upper and a lower jaw, a pivot pin positioned in said rod and pivotably connecting said jaws to each other and to said rod, to open and close said jaws, said upper and lower jaws comprising a first and a second inner surface and a first and a second peripheral shelf, respectively, said peripheral shelves undulating in-and-out in a first plane, said upper and lower jaws further comprising a first and a second array of teeth set in said first and said second peripheral shelf, respectively, said first and second arrays of teeth having tips and undulating in-and-out in the first plane, in conformance with the undulation of the first and second peripheral shelves, said first and second arrays of teeth being offset with respect to each other, said first and second peripheral shelves further comprising a first and second array of indentations offset from each other, each of said indentations being positioned to accept said tip of an associated tooth of said arrays of teeth set in the shelf of the other jaw, when said jaws are closed and wherein said first and second inner surfaces are concave.

2. The clamp of claim 1 wherein said first and second arrays of teeth are interdigitating so that each of said teeth from one array are positioned between associated teeth from the other array when said jaws are shut.

3. A clamp for use in laparoscopic surgery comprising a rod, an upper and a lower jaw, a pivot pin positioned in said rod and pivotably connecting said jaws to each other and to said rod, to open and close said jaws, said upper and lower jaws comprising a first and a second inner surface and a first and a second peripheral shelf, respectively, said peripheral shelves undulating in-and-out in a first plane, said upper and lower jaws further comprising a first and a second array of teeth set in said first and said second peripheral shelf, respectively, said first and second arrays of teeth having tips and undulating in-and-out in the first plane, in conformance with the undulation of the first and second peripheral shelves and wherein said first and second peripheral shelves and said first and second arrays of teeth also undulate up-and-down in second planes transverse to said first plane.

4. The clamp of claim 3 wherein said first and second arrays of teeth are offset with respect to each other.

5. The clamp of claim 4 wherein said first and second peripheral shelves further comprise and a first and second array of indentations offset from each other, each of said indentations being positioned to accept the tip of an associated tooth of said arrays of teeth set in the shelf of the other jaw, when said jaws are closed.

6. The clamp of claim 5 wherein said first and second inner surfaces are concave.

7. The clamp of claim 6 wherein said first and second arrays of teeth are interdigitating so that each of said teeth from one array are positioned between associated teeth from the other array, when said jaws are shut.

* * * * *